(12) United States Patent
Audigier et al.

(10) Patent No.: US 10,402,535 B2
(45) Date of Patent: Sep. 3, 2019

(54) SYSTEM AND METHOD FOR PERSONALIZED COMPUTATION OF TISSUE ABLATION EXTENT BASED ON MEDICAL IMAGES

(71) Applicants: Siemens Healthcare GmbH, Erlangen (DE); Institut National de Recherche en Informatique et en Automatique, Le Chesnay (FR)

(72) Inventors: Chloe Audigier, Valbonnes (FR); Tommaso Mansi, Plainsboro, NJ (US); Saikiran Rapaka, Pennington, NJ (US); Ali Kamen, Skillman, NJ (US); Viorel Mihalef, North Brunswick, NJ (US); Herve Delingette, La Colle sur Loup (FR); Nicholas Ayache, Nice (FR); Dorin Comaniciu, Princeton Junction, NJ (US)

(73) Assignees: Siemens Healthcare GmbH, Erlangen (DE); Institut National de Recherche en Informatique et en Automatique, Le Chesnay (FR)

( * ) Notice: Subject to any disclaimer, the term of this patent is extended or adjusted under 35 U.S.C. 154(b) by 562 days.

(21) Appl. No.: 14/622,022

(22) Filed: Feb. 13, 2015

(65) Prior Publication Data
US 2015/0242588 A1 Aug. 27, 2015

Related U.S. Application Data

(60) Provisional application No. 61/944,713, filed on Feb. 26, 2014.

(51) Int. Cl.
| | | |
|---|---|---|
| *A61B 18/12* | (2006.01) | |
| *A61B 34/10* | (2016.01) | |
| *A61B 6/03* | (2006.01) | |
| *G16H 50/50* | (2018.01) | |
| *G06F 19/00* | (2018.01) | |
| *A61B 6/00* | (2006.01) | |
| *A61B 18/00* | (2006.01) | |

(52) U.S. Cl.
CPC .............. *G06F 19/00* (2013.01); *A61B 6/032* (2013.01); *A61B 6/50* (2013.01); *A61B 6/5217* (2013.01); *A61B 18/12* (2013.01); *A61B 34/10* (2016.02); *G16H 50/50* (2018.01); *A61B 2018/00791* (2013.01); *A61B 2034/101* (2016.02); *A61B 2034/104* (2016.02); *A61B 2034/105* (2016.02)

(58) Field of Classification Search
None
See application file for complete search history.

(56) References Cited

U.S. PATENT DOCUMENTS

| | | | |
|---|---|---|---|
| 8,267,927 B2 | 9/2012 | Dalal et al. | |
| 8,295,913 B2 | 10/2012 | Haras | |
| 8,475,441 B2 | 7/2013 | Babkin et al. | |
| 8,663,083 B2 | 3/2014 | Georgi et al. | |
| 2008/0300588 A1 | 12/2008 | Groth et al. | |
| 2009/0124896 A1 | 5/2009 | Haras | |
| 2009/0142740 A1 | 6/2009 | Liang et al. | |
| 2009/0221999 A1 | 9/2009 | Shahidi | |
| 2011/0015628 A1 | 1/2011 | Dalal et al. | |
| 2011/0196385 A1 | 8/2011 | Altrogge et al. | |
| 2011/0251607 A1 | 10/2011 | Kruecker et al. | |
| 2012/0022843 A1 | 1/2012 | Ionasec et al. | |
| 2013/0158577 A1 | 6/2013 | Mahon et al. | |
| 2014/0022250 A1 | 1/2014 | Mansi et al. | |
| 2014/0136174 A1 | 5/2014 | Audigier et al. | |
| 2016/0022369 A1 | 1/2016 | Audigier et al. | |

FOREIGN PATENT DOCUMENTS

| | | |
|---|---|---|
| CN | 101563041 A | 10/2009 |
| CN | 101859341 A | 10/2010 |
| CN | 102264315 A | 11/2011 |

(Continued)

OTHER PUBLICATIONS

Audigier et al. ("Lattice Boltzmann Method for Fast Patient-Specific Simulation of Liver Tumor Ablation from CT Images" in MICCAI 2013, Part III, LNCS 8151, pp. 323-330, 2013. c Springer-Verlag Berlin Heidelberg 2013; K. Mori et al. (Eds.)).*
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.
Chinese Office Action dated Jul. 4, 2018 in corresponding Chinese Patent Application No.
Sermesant, M., et al; "An electromechanical model of the heart for image analysis and simulation." IEEE transactions on medical imaging 25.5 (2006): 612-625.25(5), pp. 612-625.
Pratt, Philip, et al; "Dynamic Guidance for Robotic Surgery Using Image-Constrained Biomechanical Models," Medical Image Computing and Computer-Assisted Intervention, Springer, Berlin, Heidelberg; pp. 77-85, XP019151689, (2010).

(Continued)

*Primary Examiner* — Lori A. Clow (57) ABSTRACT

A method and system for personalized computation of tissue ablation extent based on medical images of a patient is disclosed. A patient-specific anatomical model of the liver and liver vessels is estimated from medical image data of a patient. Blood flow in the liver and liver vessels is simulated. An ablation simulation is performed that uses a bio-heat model to simulate heat diffusion due to an ablation based on the simulated blood flow and a cellular necrosis model to simulate cellular necrosis in the liver based on the simulated heat diffusion. Personalized tissue parameters of the bio-heat model and the cellular necrosis model are estimated based on observed results of a preliminary ablation procedure. Planning of the ablation procedure is then performed using the personalized bio-heat equation and the cellular necrosis model. The model can be subsequently refined as more ablation observations are obtained.

17 Claims, 5 Drawing Sheets

(56) References Cited

FOREIGN PATENT DOCUMENTS

| CN | 102346811 A | 2/2012 |
|---|---|---|
| WO | 20140133924 A1 | 9/2014 |

OTHER PUBLICATIONS

Peng, T. et al.: "A two-equation coupled system for determination of liver tissue temperature during thermal ablation"; International Journal of Heat and Mass Transfers (2011); vol. 54; pp. 2100-2109.

O'Neill, David P. et al.: "A Three-State Mathematical Model of Hyperthermic Cell Death"; Annals of Biomedical Engineering (2011); vol. 39; No. 1, Jan. 2011; pp. 570-579.

Audigier, Chloe; et al; "Lattice Boltzmann Method for Fast Patient-Specific Simulation of Liver Tumor Ablation from CT Images"; in MICCAI 2013, Part III, LNCS 8151; pp. 323-330, 2013. c Springer-Verlag Berlin Heidelberg 2013; K. Mori et al. (Eds.)).

Sermesant, M., et al. "Patient-specific electromechanical models of the heart for the prediction of pacing acute effects in CRT: a preliminary clinical validation." Medical image analysis 16.1 (2012): 201-215.

Mansi, et al; "Data-Driven Computational Models of Heart Anatomy, Mechanics and Hemodynamics: An Integrated Framework," Biomedical Imaging (ISBI), 2012 9th IEEE Int'l. Symposium, p. 1434, XP032199297.

Hildebrand, P., et al. "Influence of operator experience in radiofrequency ablation of malignant liver tumours on treatment outcome." European Journal of Surgical Oncology (EJSO) 32.4 (2006): 430-434.

Kim, et al. "Intrahepatic recurrence after percutaneous radiofrequency ablation of hepatocellular carcinoma: analysis of the pattern and risk factors." European journal of radiology 59.3 (2006): 432-441.

Altrogge, et al. "Sensitivity analysis for the optimization of radiofrequency ablation in the presence of material parameter uncertainty." International Journal for Uncertainty Quantification 2.3 (2012), pp. 295-321.

Chen, et al. "Mathematical modeling of thermal ablation in tissue surrounding a large vessel." Journal of biomechanical engineering 131.1 (2008): 011001, 3 pages.

Jiang, et al. "Formulation of 3D finite elements for hepatic radiofrequency ablation." International Journal of Modelling, Identification and Control 9.3 (2010): 225-235.

Kröger, T., et al. "Fast estimation of the vascular cooling in RFA based on numerical simulation." The open biomedical engineering journal 4 (2010), pp. 16-26.

Payne, Stephen et al.: "Image-based multi-scale modelling and validation of radio-frequency ablation in liver tumours"; Phil. Trans. R. Soc. A (2011); vol. 369; pp. 4233-4254.

Guo, et al. "Lattice Boltzmann model for incompressible flows through porous media." Physical Review E 66.3 (2002).

Pan, et al; "An evaluation of lattice Boltzmann schemes for porous medium flow simulation." Computers & fluids 35.8-9 (2006): 898-909.

Pennes; "Analysis of tissue and arterial blood temperatures in the resting human forearm." Journal of applied physiology 85.1 (1998): 5-34.

Klinger; "Heat transfer in perfused biological tissue—I: General theory." Bulletin of mathematical biology 36.4 (1974): 403-415.

Stephen Payne, et al., "Image-based multi-scale modelling and validation of radio-frequency ablation in liver tumours," pp. 4233-4254, published Oct. 3, 2011, Philosophical Transactions of The Royal Society A (2011) 369, Retrieved from Internet URL: rsta.royalsocietypublishing.org.†

\* cited by examiner

† cited by third party

SYSTEM AND METHOD FOR PERSONALIZED COMPUTATION OF TISSUE ABLATION EXTENT BASED ON MEDICAL IMAGES

This application claims the benefit of U.S. Provisional Application No. 61/944,713, filed Feb. 26, 2014, the disclosure of which is herein incorporated by reference.

BACKGROUND OF THE INVENTION

The present invention relates to ablation therapy planning, and more particularly to patient-specific simulation of tissue ablation using medical imaging data.

In spite of recent advances in cancer therapy, treatment of primary and metastatic tumors of the abdomen, including the liver, remains a significant challenge. Hepatocellular carcinoma (HCC) for example is one of the most common malignancies encountered throughout the world (more than 1 million cases per year), with increasing frequency in western countries due to the changing prevalence of hepatitis C. For both primary liver cancer and hepatic metastases, liver resection (partial hepatectomy) is the current preferred option in patients having confined disease. In selected cases of early HCC, total hepatectomy with liver transplantation may also be considered. Unfortunately, less than 25% of patients with primary or secondary liver cancer are candidates for resection or transplantation, primarily due to tumor type, location, or underlying liver disease. Consequently, increasing interest has been focused on ablative approaches for the treatment of unresectable liver tumors or for patients not suitable for surgery. Rather than extirpation, this technique uses local in situ tumor destruction. A variety of methods have been employed to locally ablate tissue. Radiofrequency ablation (RFA) is the most commonly used, but other techniques are also used, including ethanol injection, cryo-therapy, irreversible electroporation, and microwave ablation.

The RFA procedure is performed by placing a probe within or near the malignant tissue. Electrodes at the tip of the probe create heat, which is conducted into the surrounding tissue, causing coagulative necrosis at temperatures above 50° C. In order to prevent recurrence, the RFA procedure is considered to be successful if the generated necrosis area fully covers the tumor. To place the probe at the target location, the physician relies on intra-operative imaging techniques, such as ultrasound. However, the success of the procedure depends on the optimal placement of the probe and heat delivery with respect to the circulation system and tissue properties of the liver and tumors. The success of ablation is further challenged by the hepatic blood vessels that dissipate heat, thus potentially reducing RFA efficiency. Different placements may have different results, and it is sometimes necessary to combine successive ablations for an optimal procedure.

BRIEF SUMMARY OF THE INVENTION

The present invention provides a method and system for personalized planning and guidance of tumor ablation using medical images. Embodiments of the present invention focus on liver tumors and model the effects of ablation including heat diffusion and convection, cellular necrosis, and blood flow through the vessels and liver, with special focus on the estimation of model parameters from patient data such that the model captures patient's liver reaction to heat. Starting from a medical image of a patient, such as a computed tomography (CT) or magnetic resonance imaging (MRI) image, embodiments of the present invention estimate tissue parameters involved in heat transfer from patient data to perform individualized simulations of liver tumor radio-frequency ablation (RFA) for the patient. The personalization step is beneficial as tissue properties may vary among individual and due to disease (e.g. cirrhotic, fatty, tumor, etc.). The forward model of RFA, which relies on patient medical images, is based on a computational model of heat diffusion, cellular necrosis, and a blood flow solver which simultaneously model blood circulation in the liver vessels and the liver parenchy. Embodiments of the present invention estimate the patient-specific tissue parameters using an optimizer such that the simulated destroyed tumor tissue matches an observed lesion. The patient-specific tissue parameters can then be used to plan additional ablations for other lesions or ablation refinement of the current lesion by simulating different ablation strategies. The model can also be iteratively refined as more ablations are performed, for more and more accurate pre-ablation planning. Embodiments of the present invention can also be similarly employed to match simulated and measured temperature maps in addition to or instead of lesions. Embodiments of the present invention display the estimated patient-specific tissue parameters along with patient-specific temperature diffusion maps, cellular necrosis maps and virtual probe locations and parameters yielding the simulated ablation maps.

In one embodiment of the present invention, a patient-specific anatomical model of the liver parenchyma and vessels is estimated from medical image data of a patient. A patient-specific bio-heat model combining blood flow in the liver parenchyma and vessels, heat diffusion, and cellular necrosis in the liver is estimated based on simulated ablation results and a first ablation observation. One or more virtual ablations for the patient are performed using the patient-specific bio-heat model. A visualization of simulated necrosis resulting from the one or more virtual ablations is generated.

These and other advantages of the invention will be apparent to those of ordinary skill in the art by reference to the following detailed description and the accompanying drawings.

DETAILED DESCRIPTION

The present invention relates to patient-specific modeling and simulation of tumor ablation using medical imaging data for therapy planning and guidance. Embodiments of the present invention are described herein to give a visual understanding of the methods for patient-specific modeling and simulation using medical imaging data, exemplified on the case of liver tumor. However, the same approach could be employed to other tumors that can be treated through ablation therapy. The proposed invention could also apply to other ablation techniques that rely on heat delivery. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored locally or remotely and accessed by the computer system.

Embodiments of the present invention utilize a computational model for patient-specific simulation of heat transfer and cellular death during radio frequency ablation (RFA) based on patient-specific anatomies and tissue parameters estimated from medical images and measurements, such as computed tomography (CT), magnetic resonance images (MRI), rotational angiography, or ultrasound (US). When no temperature map is available, the model can be adjusted from a conservative ablation performed on the patient. The information from the ablation performed on the patient is then used to personalize parameters of the computational model for a more refined, targeted ablation or an additional ablation when several lesions need to be treated. This approach is therefore suitable to multi-stage ablation procedures. Moreover, the personalization can be refined as more ablations are performed. Embodiments of the present invention utilize the Lattice Boltzmann Method (LBM) to compute not only heat diffusion and cellular necrosis, but also blood and parenchyma flow in the liver tissue. The computation of the blood flow in the liver tissues is based on a computational fluid dynamics (CFD) solver that incorporates a spatially-varying porous part to deal with the liver parenchyma and the large vessels simultaneously.

Embodiments of the present invention provide a method for fast patient-specific simulation of liver tumor ablation that can be utilized interactively in a clinical setting. The LBM implementation for solving the bio-heat equation provides high parallel scalability, and therefore can be implemented on a massively parallel architecture, such as a graphics processing unit (GPU). Using such a parallel implementation, liver tumor ablation simulations can be performed efficiently in response to user interactions, which allows a user to interactively plan liver tumor ablation therapy using the simulations in a clinical setting, prior to effectively delivery the ablation therapy. The computational efficiency of the solver also allows interventional use of the system, where the clinician performs mini-planning before each ablation to optimize therapy delivery. At each step, the model can potentially be refined based on observed ablation results for more accurate planning.

Figure 1:
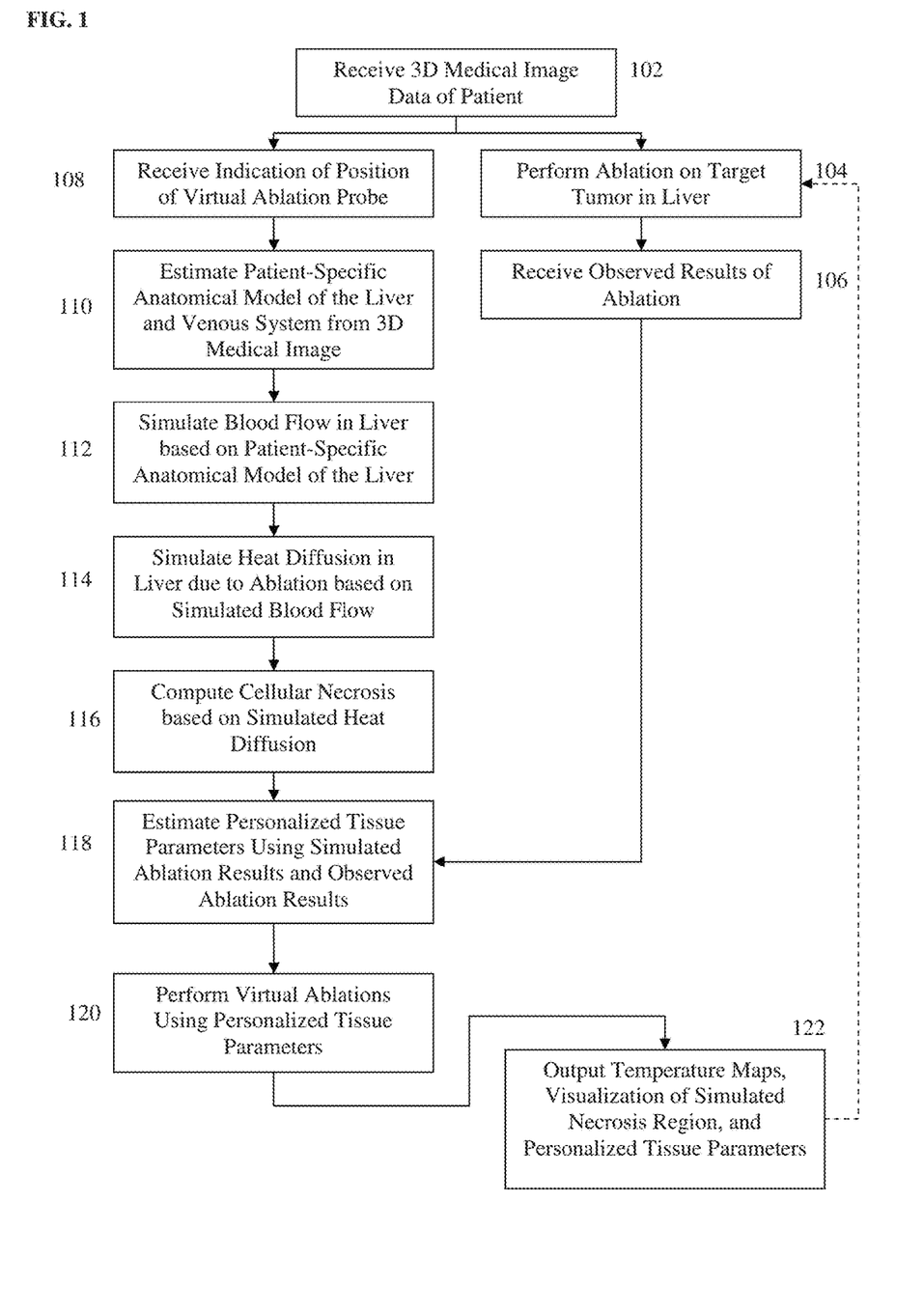
FIG. 1 illustrates a method for patient-specific planning and therapy guidance of liver tumor ablation according to an embodiment of the present invention.

FIG. 1 illustrates a method for patient-specific simulation of liver tumor ablation according to an embodiment of the present invention. The method of FIG. 1 transforms medical image data representing a patient's liver anatomy to estimate personalized tissue parameters for the patient and to provide patient-specific simulation of liver tumor ablation. At step 102, 3D medical image data of at least a liver region of a patient is received. The pre-operative 3D image data can be acquired using any type of medical imaging modality, such as computed tomography (CT), three-dimensional rotational angiography, magnetic resonance imaging (MRI), ultrasound (US), positron emission tomography (PET), etc., provided that the region of the liver to be treated is visible in the medical image data. The medical image data can be received directly from an image acquisition device, such as a CT scanner, a C-arm image-acquisition device, an MRI scanner, or an US scanner, or received by loading previously stored image data of the patient (acquired pre-operatively). In a possible embodiment, the patient may receive a contrast agent that is generally opaque to x-rays. The contrast agent collects or is in the circulatory system, so vessels contrast with tissue.

At step 104, an ablation procedure is performed on a target tumor location in the liver of the patient. The ablation procedure is an actual RF ablation performed on a patient by placing an ablation probe a location in the patient's liver corresponding to a target tumor. Electrodes at the tip of the probe create heat, which is conducted into the surrounding tissue, causing cellular necrosis of the surrounding tissue. It is to be understood that the actual ablation procedure performed in step 104 of FIG. 1 and the ablation simulation performed in steps 108-116 can be performed in any order. For example, in one possible implementation, the ablation procedure of step 104 can be independent of the ablation simulation of steps 108-116 and the ablation procedure of step 104 can performed prior to, simultaneously to, or after the ablation simulation of steps 108-116. In another possible implementation, the ablation simulation of steps 108-116 can be performed prior to the ablation procedure of step 104 and the results of the ablation simulation (e.g., temperature diffusion maps and cellular necrosis maps) can be used to guide the ablation procedure of step 104.

At step 106, observed results of the ablation procedure are received. For example, the observed results of the ablation procedure can include a cellular necrosis map showing a cellular necrosis region resulting from the ablation procedure, and/or temperature diffusion maps showing temperature diffusion in the liver tissue over time resulting from the ablation procedure. The observed results of the ablation procedure may also include temperature measurements at the tip of the ablation probe, or other data that reflects the temperature in the liver tissue, such as strain imaging using ultrasound or delivered power tracings. The observed results of the ablation procedure may also include medical images of the patient acquired after the ablation procedure is performed. In an exemplary implementation, observed results, such as an observed necrosis region, can be extracted from post-ablation medical images, for example by manually or automatically segmenting the necrosis region in the post-ablation medical images.

At step 108, an indication of a position of a virtual ablation probe is received. In one embodiment, a user indication of a placement position of the ablation probe is received. The ablation is to occur near or in a lesion (e.g., tumor) or other region of tissue. Given anatomy, type of ablation, type of ablation device, or other limitations, the placement in the tissue may be limited. According to an advantageous embodiment, the position of the virtual ablation probe corresponds to the position of the ablation probe at the location of the target tumor in the ablation procedure of step 104. The user may indicate a possible placement of the ablation probe by selecting a location or locations in the medical image data. For example, a location in a displayed multi-planar reconstruction of the patient can be selected by a user using an input device, such as a mouse, touch screen, etc. Although in FIG. 1, receiving an indication of the position of the virtual ablation probe (step 108) is shown as before the estimation of the patient-specific anatomical model from the medical image (step 110), it is to be understood that these steps can occur in either order or concurrently. In addition to the position of the virtual ablation probe, the user may also input a spatial extent of the ablation probe, the type of ablation, duration, an indication of the spatial extent of the tumor, an indication of a location in the tumor, an amount of power for ablation, a type of ablation device, a sequence of power, and/or other characteristic of the ablation or tissue. These inputs should correspond to the ablation probe used and the ablation performed in the ablation procedure of step 104. Various inputs may be automated, such that instead of user input, a processor provides the necessary information. For instance, a processor can automatically test different probe locations in the vicinity of the tumor and provide the user a suggestion of the position yielding optimal tumor ablation coverage.

At step 110, a patient-specific anatomical model of the liver and the circulatory system in the liver is estimated from the 3D medical image data. The patient-specific anatomical model is a detailed anatomical model of the patient's liver parenchyma, tumors, hepatic veins, vena cava, and portal vein. If visible, the hepatic artery and/or the biliary system can also be segmented. The 3D surface of the liver may be segmented automatically from the 3D medical image data. In one embodiment, the patient-specific anatomical model is semi-automatically estimated from the CT data using a graph theory approach, such as random walker segmentation. For each structure (parenchyma, tumors, hepatic veins, vena cava, portal vein, and hepatic artery), the user defines seeds inside and outside the area of interest. Then, the random-walker algorithm automatically estimates the boundary of the structure. The process may be refined by the user, interactively, if necessary. From the segmentation, a level set representation of the liver, minus the tumor and vessels, is calculated. Next, the resulting segmentations are merged into a multi-label mask image, which is then used to generate a tetrahedral multi-domain mesh. A porosity map is then calculated for the mesh model of the liver. In an exemplary implementation, the porosity map is created by setting the porosity to 1 in the visible vessels and to 0.1 in the parenchyma, 1 being infinite porosity (i.e. free flow circulation), and 0 meaning no porosity (i.e. no flow circulation at all). A layer of porosity 0.01 can also be added in between the visible vessels and the parenchyma to model vessel walls and prevent free-flow from leaking laterally from the vessels. This additional layer of porosity can be added by using a 26 connectivities dilatation of the vessel voxels and manually detecting the vessel inlets and outlets.

Figure 2:
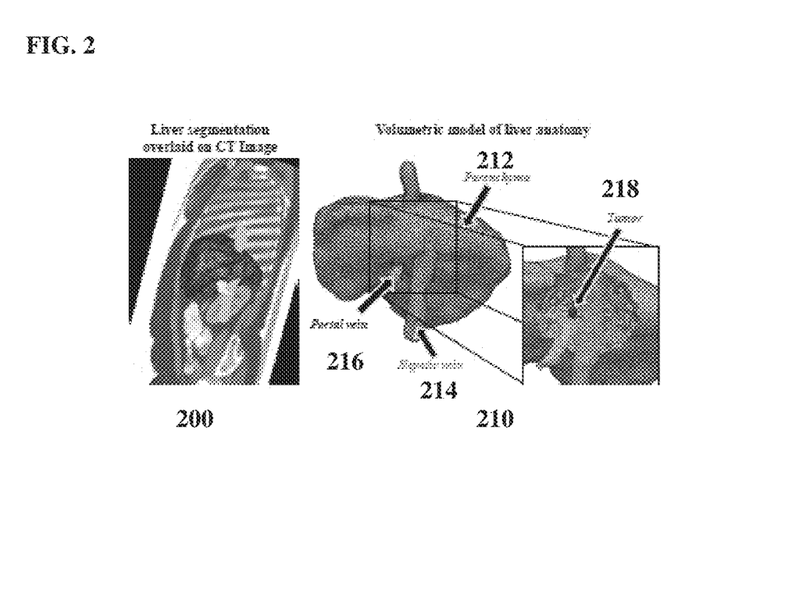
FIG. 2 illustrates exemplary results for estimating a patient-specific anatomical model of the liver.

FIG. 2 illustrates exemplary results for estimating a patient-specific anatomical model of the liver. As shown in FIG. 2, image 200 shows the liver segmentation overlaid on a CT image. Image 210 shows a tetrahedral volume mesh generated from the liver segmentation, including the parenchyma 212, hepatic vein 214, portal vein 216, and a segmented tumor 218. In an alternative embodiment, each structure is directly rasterized on the computational domain without using an intermediate tetrahedral mesh.

Returning to FIG. 1, at step 112, blood flow in the liver is simulated based on the patient-specific anatomical model of the liver and venous system. The blood flow through the venous system of the liver acts as a heat sink in diffusing the heat applied by the ablation probe. The blood flow in the patient-specific anatomic model is simulated in order to provide a personalized modeling of the heat sink due to the blood flow. Locations of the vessels in the tissue region, the size of the vessels, and/or other vessel characteristics are used to model the heat sink characteristics in the region of interest. The characteristics may be extracted from the segmented vessel information in the patient-specific anatomical model of the liver.

In a possible implementation, the blood flow in the main vessels and the parenchyma can be computed separately as described in International Publication No. WO 2014/133924 A1, entitled "System and Method for Interactive Patient Specific Simulation of Radiofrequency Ablation Therapy," which is incorporated herein in its entirety by reference. However, this can lead to difficulties in setting proper boundary conditions, in particular at the outlets and inlets inside the parenchyma. In an advantageous embodiment, both phenomena (blood flow in the vessels and in the parenchyma) are computed together through a generalized 3D incompressible Navier-Stokes equation for fluid flow in porous media. In particular, with v denoting the blood velocity inside the liver, the blood flow can be simulated by solving:

$$\frac{dv}{dt} + v \cdot \nabla v = -\frac{1}{\rho} \nabla p + \mu_e \nabla^2 \cdot v + F \qquad (1)$$

$$F = -\frac{\mu(1-\epsilon)^2}{\alpha^2 \epsilon^2} v$$

where p is the pressure, ρ is the fluid density, and the added force F represents a spatially varying body force modeling the presence of a porous medium.

Figure 3:
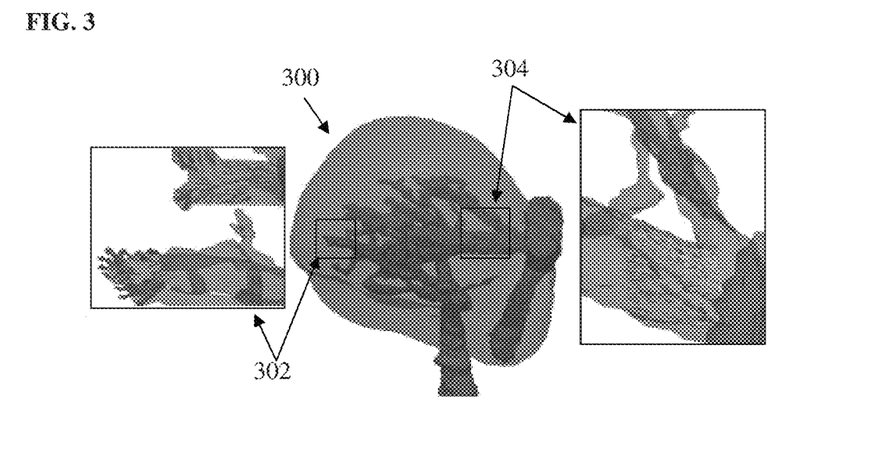
FIG. 3 illustrates results of an exemplary blood flow simulation in patient-specific anatomical model of the liver.

The porous force F depends on the porosity ∈, a value comprised between 0 and 1 that defines the level of porosity, 1 being free-flow circulation (infinite porosity) and 0 being blocked flow circulation (no porosity). In a preferred embodiment, ∈ is set to 1 in the vessels visible in the medical image data (e.g., CT image) and set to 0.1 in the parenchyma, modeled then as a porous medium. It is also possible that porosity can vary spatially. At the border of the liver, no flux boundary conditions are used, whereas Dirichlet boundary conditions are applied at the inlets of the portal vein and the vena cava and at the outlet of the vena cava, and similarly for the hepatic artery if available. The portal vein and vena cava inflow are fixed as well as the outlet pressure. In an alternative embodiment, the inflow is obtained through flow measurements (Color Doppler, phase-contrast MRI) and/or the outlet pressure measured invasively through catherization or set to population average. Using this method only the inlet of the large vessels are needed to set the boundary conditions. FIG. 3 illustrates results of an exemplary blood flow simulation in patient-specific anatomical model of the liver 300. Image 302 shows zoomed-in blood flow simulation results at the extremities of the hepatic veins and image 304 shows zoomed-in blood flow simulation results inside the vena cava and the portal vein.

According to an advantageous embodiment, the Lattice Boltzmann method (LBM) is used rather than the finite element method (FEM) in order to discretize equation (1), since LBM leads to faster computation on regular grids using a graphics processing unit (GPU). However, the present invention is not limited to LBM and other techniques, such as FEM, finite volume elements or finite difference elements can be used as well. A computational domain is first generated for the patient-specific anatomical model. For example, the computational fluid dynamics (CFD)-Porous model can be solved on an isotropic Cartesian grid using LBM with 19-connectivity topology and Neumann boundary conditions. For stability reasons, a Multiple- Relaxation-Time model can be used. The governing equation at position x=(x,y,z) for the edge $e_i$ is given by:

$$f(x+e_i\Delta x, t+\Delta t) = f(x,t) + A[f^{eq}(x,t) - f(x,t)] + \Delta t g(x,t), \quad (2)$$

where $f(x) = \{f_i(x)\}_{i=1 \ldots 19}$ is the vector of distribution functions with $f_i(x)$ being the probability of finding a particle travelling along the edge $e_i$ of the node x at a given time t, $c = \Delta x/\Delta t$, $c_s^2 = 1/4$, and $\Delta x$ is the spacing of the Cartesian grid.

$$f_i^{eq}(x, t) = \omega_i \rho \left[ 1 + \frac{e_i \cdot v}{cc_s^2} \right]$$

and $\omega = \{\omega_i\}_{i=1 \ldots 19}$ is the vector of weighting factors.

$$g(x, t) = \omega_i \rho \frac{e_i \cdot F}{c_s^2}.$$

The fluid density $\rho$ and the velocity v are computed as $\rho = \sum_{i=1}^{19} f_i(x, t)$ and $$\rho v = \sum_{i=1}^{19} e_i f_i(x, t) + \frac{\Delta t}{2} \rho F$$

and are updated at every node of the grid for every timestep.

Returning to FIG. 1, at step 114, heat diffusion in the liver due to ablation is computed based on the simulated blood flow and the location of the virtual ablation probe. The diffusion of heat over time in the liver tissue is simulated by calculating the diffusion or progression of temperature change over time. The diffusion of heat is computed using a heat diffusion model that describes how the heat flows from the virtual ablation probe location through the liver while accounting for the cooling effect of the main vessels and parenchyma. A temperature distribution field is solved as a function of time using a partial differential equation or other equation. The numerical solution of the bio-heat transfer equations yields an underlying temperature distribution field that varies in space and time. Computing heat diffusion in biological tissue amounts to solving the coupled bio-heat equations derived from the theory of porous media, where each elementary volume is assumed to comprise a tissue fraction and a blood fraction. Two main simplifications for solving the coupled bio-heat equations are the Pennes model and the Wulff-Klinger (WK) model.

In the Pennes model, the blood temperature is assumed constant, which holds close to large vessels, where blood velocity is high. The Pennes model is expressed as:

$$(1-\varepsilon)\rho_t c_t \frac{\partial T}{\partial t} = (1-\varepsilon)Q + (1-\varepsilon)\nabla \cdot (d_t \nabla T) + H(T_{b0} - T) \quad (3)$$

In the Wulff-Klinger model, equilibrium between tissue and blood temperatures is assumed ($T_t = T_b$), with a small blood volume fraction $\varepsilon$. This model is therefore well-suited for small vessels, where blood velocity is low. The Wulff-Klinger model can be expressed as:

$$(1-\varepsilon)\rho_t c_t \frac{\partial T}{\partial t} = (1-\varepsilon)Q + (1-\varepsilon)\nabla \cdot (d_t \nabla T) + \varepsilon \rho_b c_b v \cdot \nabla T \quad (4)$$

In the above equations, T is the temperature, Q is the source term, v is the blood velocity, and $T_{bo}$ is the mean temperature of the blood in larger vessels (assumed constant). Subscripts t and b refer to tissue and blood phases respectively. Definitions and exemplary initial values of the remaining model parameters are provided in Table 1, below.

| parameter | description | value |
|---|---|---|
| $\rho_b, \rho_t$ | blood and tissue densities | $1.06 \times 10^3$ kg m$^{-3}$ |
| $c_b$ | blood heat capacity | $4.18 \times 10^3$ J(kg K)$^{-1}$ |
| $c_t$ | tissue heat capacity | $3.6 \times 10^3$ J(kg K)$^{-1}$ |
| $c_t^*$ | tissue heat capacity in dead cells | $0.67 \times 10^3$ J(kg K)$^{-1}$ |
| $d_b, d_t$ | blood and tissue heat conductivities | $0.512 \times (1 + 0.00161 \times (T - 310))$ W(m K)$^{-1}$ |
| H | connective transfer coefficient | $24.4 \times 10^4$ W (m$^3$ K)$^{-1}$ |
| $\varepsilon$ | blood volume fraction | 0.1 |
| k | permeability | $4.0 \times 10^{-11}$ m$^2$ |
| $\mu$ | dynamic viscosity of the blood | 0.0035 Pas |
| $k_f$ | forward rate constant | $3.33 \times 10^{-3}$ s$^{-1}$ |
| $k_b$ | backward rate constant | $7.77 \times 10^{-3}$ s$^{-1}$ |
| $T_k$ | parameter of cell state model | 40.5° C. |

The main difference between the Pennes and the Wulff-Klinger models lies in their cooling terms (i.e., the last term of the right-hand side). The former acts as a volumetric homogeneous heat sink whilst the latter accounts for the directional effect of blood flow on the tissue temperature field. Therefore, both equations can be easily implemented in a modular way to cope with tissue in homogeneity, by using one or the other cooling term.

Current imaging techniques may not allow estimation of an accurate ratio between blood and liver tissue. Large vessels are clearly identified in the patient-specific anatomical model of the liver, but small capillaries are difficult to image. Therefore embodiments of the present invention solve the bio-heat equation by combining the Pennes and Wulff-Klinger models in a unified and modular framework to model large and small vessels. Assuming that blood vessels and the surrounding tissue are isolated from each other, the liver temperature T is calculated by solving the diffusion equation:

$$\rho_t c_t \partial T/\partial = Q + \nabla \cdot (d_t \nabla T) \quad (5)$$

everywhere in the domain, to which the cooling term $H(T_{b0} - T)/(1-e)$ is added when a point belongs to a large vessel (Pennes model) and the cooling term $-\varepsilon \rho_b c_b v \cdot \nabla T/(1-\varepsilon)$ is added when a point belongs to a small vessel or the parenchyma (Wulff-Klinger model). When arriving in step 114 for the first time, the heat diffusion simulation is performed using nominal values taken from the literature for the tissue parameters of the heat diffusion model (Table 1).

The parameters are then optimized in order to personalize the tissue parameters for the patient in step 118. According to an advantageous embodiment, the bio-heat model is solved on an isotropic Cartesian grid using the Lattice Boltzmann method (LBM) with a no-flux boundary condition on the liver boundary defined as a level-set function. The heat source term is modeled through a Dirichlet boundary condition at the location of the virtual probe. For example, in an exemplary implementation the heat source term is modeled through a Dirichlet boundary condition of 100° C. (or a temperature corresponding to the temperature of the actual ablation probe used in the ablation procedure of step 104) at the location of the virtual probe. In an alternative embodiment, the heat source delivered by the probe could be modeled.

At step 116, cellular necrosis in the liver is simulated based on the simulated heat diffusion. Heat from an ablation probe can cause cellular necrosis in the liver. In one embodiment, the tissue damage is modeled as using a three state model. The model computes the variation of concentration of live cells (A), vulnerable cells (C), and dead cells (D) over time according to the state equation:

where $k_f$ and $k_b$ are the rates of cell damage and recovery, respectively. In particular, $k_f$ depends on the temperature through the equation: $k_f = \bar{k}_f e^{T/T_k}(1-A)$ with $\bar{k}_f$ being a scaling constant and $T_k$ a parameter that sets the rate of the exponential increase with temperature. This equation results in three simultaneous ordinary differential equations that can be solved with a first order explicit scheme at each vertex of the Cartesian grid, yielding a spatially-varying cell state field that is then used in the LBM solver. In an exemplary implementation, the initial conditions can be chosen as A=0.99, V=0.01 and D=0.00. Exemplary initial values for the parameters $k_b$, $\bar{k}_f$, and $T_k$ are shown in Table 1, above. Additionally, dead or damaged cells do not have the same heat capacity $c_t$ as live cells. This phenomenon can affect heat transfer and ablation extent. Accordingly, at each time step of the heat diffusion simulation, the state of the cell is updated at each point given the cell's current temperature, and the heat capacity of the cell is updated based on the state of the cell. The heat capacity $c_t$ is used if the cell is healthy or vulnerable, and the heat capacity $c_t^*$ is used for dead cells. Exemplary initial values for $c_t$ and $c_t^*$ are shown in Table 1. The values of the parameters of the cellular necrosis model are optimized in step 118 in order to personalize these values for the patient.

At step 118, personalized tissue parameters for the heat diffusion and cellular necrosis models are estimated based on the simulated ablation results (from steps 114 and 116) and the observed ablation results (from step 106). As described above, the parameters in the heat diffusion and cellular necrosis models can be initialized using values from the literature. These values are then personalized for the patient using the observed results of the ablation procedure performed on the patient. According to an advantageous implementation, the extent of the observed necrosis region can be used to personalize the parameters, as temperature maps resulting from the ablation procedure are often not available. If temperature maps are available, they can also be used for personalization in a similar way. Most of the tissue parameters of the heat diffusion model and the cellular necrosis model are defined as constant, whereas the tissue diffusivity $d_t$ and heat capacity $c_t$ are temperature dependent and therefore spatially distributed. A sensitivity analysis can be performed to determine which parameters most heavily influence the shape of the simulated necrosis area. The most sensitive parameters are then selected for personalization, and optimized to minimize the average point-to-point mesh error between the simulated cellular necrosis region and the observed necrosis region. By performing a sensitivity analysis, the present inventors have determined that the tissue diffusivity $d_t$ and the damage rate coefficient $\bar{k}_f$ term of the cell state model most heavily influence the volume and maximum diameter of the simulated necrosis area. According to an advantageous embodiment, the tissue diffusivity $d_t$ and the damage rate coefficient $\bar{k}_f$ term of the cell state model are optimized to minimize the average point-to-point mesh error between the simulated cellular necrosis region and the observed necrosis region in order to estimate personalized values for these parameters for the patient. It should be noted though that the approach could be employed without any change to other model parameters. At each iteration of the optimization, the tissue parameters are adjusted to reduce the average point-to-point mesh error between the simulated cellular necrosis region and the observed necrosis region, and the ablation simulation is repeated to generate a new simulated necrosis area. These steps can be repeated until the average point-to-point mesh error between the simulated cellular necrosis region and the observed necrosis region is less than a threshold. Other metrics can be employed to compare the simulated necrosis region and the observed necrosis region, like volume, shape metrics, or Hausdorff distances. According to an exemplary implementation, a gradient-free optimization method, such as the Constrained Optimization BY Linear Approximations (COBYLA) method, which only requires a few hundred iterations of forward simulation, can be used to optimize the tissue parameters. Once the personalized tissue parameters are estimated, the personalized tissue parameters can be output, for example, by displaying these tissue parameters on a display device and/or storing the tissue parameters on a storage or memory of a computer system. In addition, temperature maps and/or visualizations of the simulated cellular necrosis area for any or all of the ablation simulations may be displayed as well.

As described above, the observed necrosis area resulting from the ablation procedure can be used to optimize the tissue parameters of the heat diffusion model and the cellular necrosis model in order to estimate the personalized parameters. However, the present invention is not limited thereto. Temperature maps resulting from the ablation procedure, if available, may also be used to estimate the personalized parameters, as well temperature data measured directly at the tip of the ablation probe, or other surrogates for temperature, such as strain imaging data acquired using ultrasound or delivered power traces.

Figure 4:
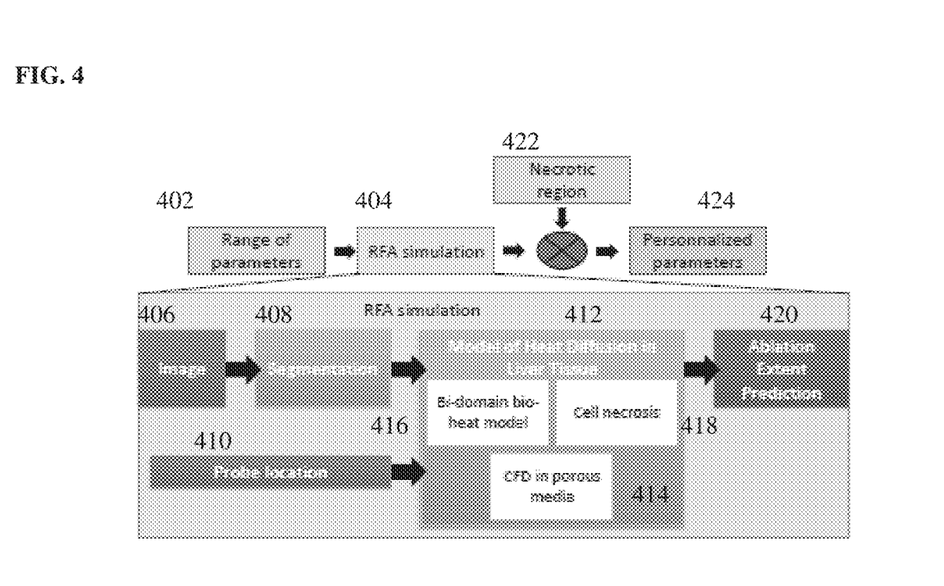
FIG. 4 illustrates a framework for estimating personalized tissue parameters for ablation simulation according to an embodiment of the present invention.

FIG. 4 illustrates a framework for estimating personalized tissue parameters for ablation simulation according to an embodiment of the present invention. The framework of FIG. 4 provides an illustration of steps 102-118 of FIG. 1. As illustrated in FIG. 4, an initial range of parameters 402 is input and a RFA simulation 404 is performed. In the RFA simulation 404, a medical image 406 of the patient is input, and segmentation 408 is performed on the medical image 406 to generate a patient-specific anatomical model of the liver. The patient-specific anatomical model of the liver and a probe location 410 are input and heat diffusion in the liver tissue is modeled 412. The heat diffusion in the liver tissue is modeled using CFD in porous media 414 to simulate blood flow in the liver, a bi-domain bio-heat model 416, and a cellular necrosis model 418, and results in an output of a simulated ablation extent (e.g., cellular necrosis area) prediction 420. The simulated ablation extent prediction 420 is compared to an input observed necrotic region 422, and tissue parameters of the bio-heat model 416 and the cellular necrosis model 418 are optimized to minimize an error between the simulated ablation extent prediction 420 and the observed necrotic region 422, resulting in personalized parameters 424, which are output.

Returning to FIG. 1, at step 120, additional virtual ablations are performed using the personalized tissue parameters. Once the personalized tissue parameters for a patient are estimated for the patient in step 118, these personalized tissue parameters can be used to simulate additional ablations for the patient. For example, the personalized tissue parameters can be considered to be spatially invariant within the same patient and thus can be used in the heat diffusion model and the cellular necrosis model in order to simulate ablations in additional tumors in the patient's liver. The personalized tissue parameters can also be used to simulate an ablation to refine the ablation of the same tumor. Such simulations can predict the temperature diffusion and necrosis region for various ablations and can be used to select ablation locations and durations to plan and guide actual ablation procedures. The additional virtual ablations can be interactive, such that a user can input various virtual ablation probe positions and a respective ablation simulation is performed for each of the user input virtual probe locations. A weak coupling model can be used to perform the additional virtual ablations. That is, since the blood flow has an influence on the temperature distribution through the WK model but the temperature does not affect the blood flow (coagulation is not considered here), the simulation calculations can be sped up by only computing the blood flow distribution once. Accordingly, the blood flow distribution determined in the blood flow simulation of step 112 can be used for all the additional simulations, with each of the additional simulations being performed by performing the simulation of the heat diffusion (step 114) and the simulation of the cellular necrosis (step 116) for the corresponding probe location using the personalized tissue parameters.

At step 122, temperature maps and a visualization of a simulated necrosis area for each of the additional ablation simulations are output. The personalized tissue parameters for the patient can also be output. For example, the temperature maps and simulated necrosis area visualization can be output by displaying the temperature maps and simulated necrosis area visualization on a display of a computer system using color coding, streamlines or iso-contours. The temperature map can be updated at every time step or every N time steps to show the dynamics of the system and the variation of the temperature in the liver over time. The visualization of the cellular necrosis area can be a visualization of the final simulated cellular necrosis area for a virtual ablation or can be a cellular necrosis map that is updated at every time step or every N time-steps to show the variation of the simulated cellular necrosis area over time.

As discussed above, the additional virtual ablations can be used to plan and guide subsequent ablation procedures. In particular, once a virtual ablation is performed by simulating an ablation, an actual ablation procedure corresponding to the virtual ablation can then be performed. The physician performing the actual ablation procedure can be guided by the virtual ablation to position the actual ablation probe in a location corresponding to that of the virtual ablation probe in the virtual ablation. In this case, the method of FIG. 1 may return to step 104 and perform the actual ablation procedure and then receive the results of the ablation procedure (step 106). Once the actual ablation procedure corresponding to the simulated virtual ablation is performed, the method can then return to step 118 to refine the personalized tissue parameters by further optimizing the personalized tissue parameters using results from the virtual simulation and the corresponding ablation procedure. This can lead to a clinical workflow in which, during an intervention, the clinician performs a small ablation, an image of the resulting cellular necrosis region (or a temperature map resulting from the ablation) is acquired, and the personalized tissue parameters of the bio-heat model and the cellular necrosis model are estimated. The clinician then does virtual ablation using the personalized model parameters, and uses the virtual ablation to guide the real ablation. Based on the accuracy of the virtual ablation with respect to the real ablation guided by the virtual ablation, the personalized tissue parameters can then be further refined, and subsequent additional virtual ablations and corresponding real ablations can be performed.

Figure 5:
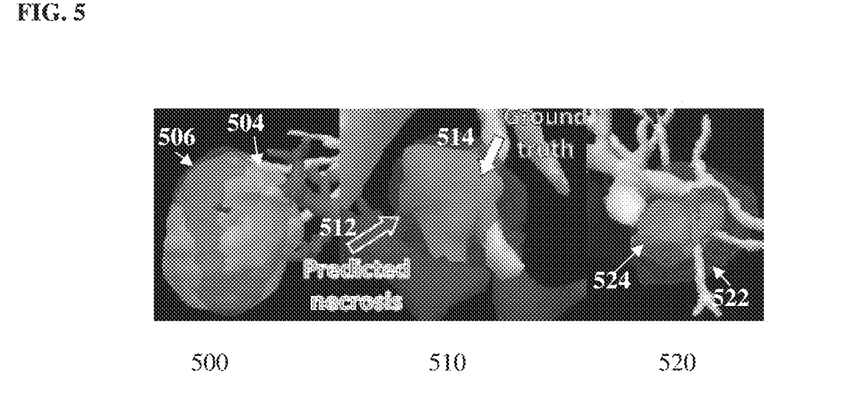
FIG. 5 illustrates exemplary results of ablation simulations using personalized parameters.

FIG. 5 illustrates exemplary results of ablation simulations using personalized parameters. As shown in FIG. 5, image 500 shows the simulated necrosis region 502 and an observed necrosis region 504 for a first tumor in a patient after the tissue parameters of tissue diffusivity $d_t$ and the damage rate coefficient $\bar{k}_f$ were optimized to minimize an error between the simulated necrosis region 502 and an observed necrosis region 504 to generate personalized parameters. Image 510 shows a predicted necrosis region 512 for a second tumor of the patient generated using an ablation simulation with the personalized parameters, and a ground truth necrosis region 514 for the second tumor. Image 520 shows a predicted necrosis region 522 for a third tumor of the patient generated using an ablation simulation with the personalized parameters, and a ground truth necrosis region 524 for the third tumor.

Figure 6:
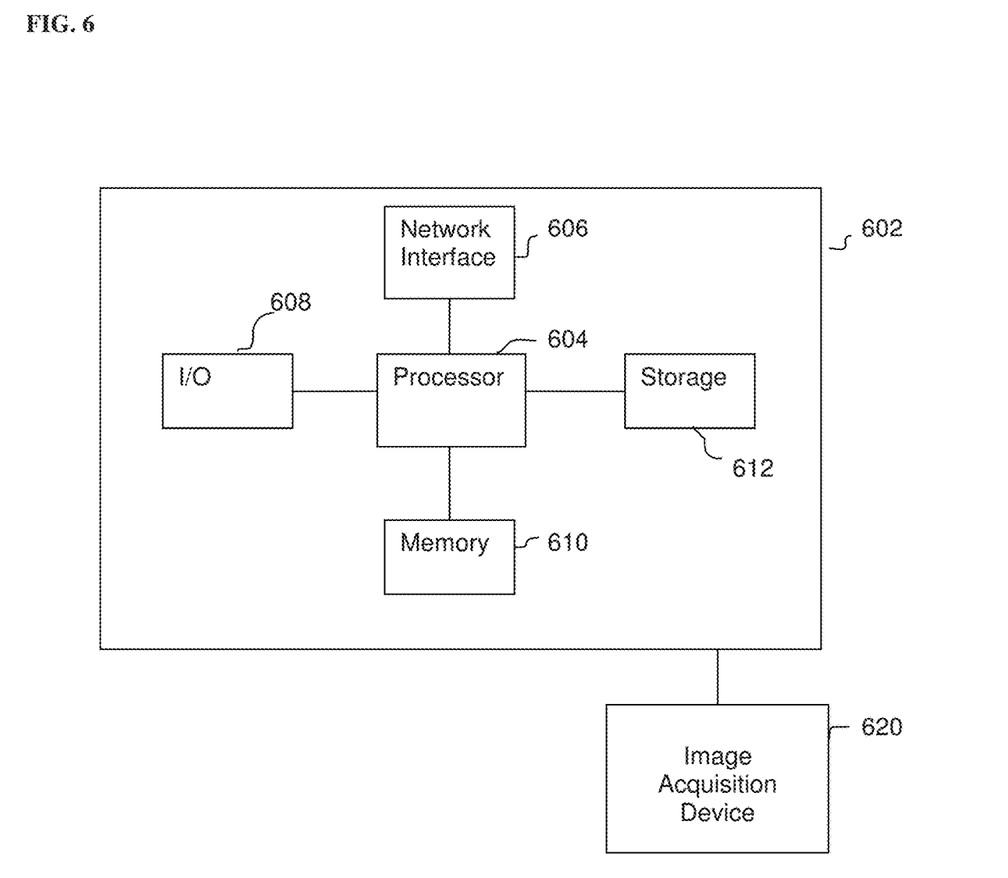
FIG. 6 is a high-level block diagram of a computer capable of implementing the present invention.

The above-described methods for patient-specific simulation of liver tumor ablation and estimation of personalized tissue parameters for a patient can be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIGS. 1 and 4 may be defined by the computer program instructions stored in the memory 610 and/or storage 612 and controlled by the processor 604 executing the computer program instructions. An image acquisition device 620, such as a CT scanning device, C-arm image acquisition device, MR scanning device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for patient-specific planning and model-based guided liver tumor ablation therapy using a personalized model, comprising:
   receiving, in response to a first actual ablation procedure performed on a target liver tumor of a patient, a first observed ablation result;
   estimating a patient-specific anatomical model of a liver parenchyma and vessels from medical image data of the patient;
   estimating personalized tissue parameters for a bio-heat model that simulates blood flow in the liver parenchyma and vessels, heat diffusion, and cellular necrosis in the liver by adjusting one or more tissue parameters of the bio-heat model to minimize an error between simulated ablation results generated using the bio-heat model and the first observed ablation result;
   performing one or more virtual ablations for the patient using the bio-heat model with the personalized tissue parameters;
   generating a visualization of simulated necrosis resulting from the one or more virtual ablations; and
   performing a second actual ablation procedure based on at least one of the one or more virtual ablations.

2. The method of claim 1, further comprising:
   refining the estimated personalized parameters of the bio-heat model based on simulation results of the one or more virtual ablations and one or more second observed ablation results resulting from the second actual ablation procedure.

3. The method of claim 1, wherein performing one or more virtual ablations for the patient using the bio-heat model with the personalized tissue parameters comprises:
   performing the one or more virtual ablations for the patient using the bio-heat model with the personalized tissue parameters based on user input ablation location, deployment, and device parameters.

4. The method of claim 1, wherein estimating personalized tissue parameters for a bio-heat model that simulates blood flow in the liver parenchyma and vessels, heat diffusion, and cellular necrosis in the liver by adjusting one or more tissue parameters of the bio-heat model to minimize an error between simulated ablation results generated using the bio-heat model and the first observed ablation result comprises:
   simulating blood flow in the liver parenchyma and vessels based on the patient-specific anatomical model;
   simulating the heat diffusion due to an ablation based on a virtual ablation probe position and the simulated blood flow in the liver parenchyma and vessels by solving the bio-heat model at each of a plurality of nodes of a computational domain corresponding to the patient-specific anatomical model of the liver parenchyma and vessels;
   simulating cellular necrosis in the liver based on the simulated heat diffusion using a cellular necrosis model that computes a cellular state at each of the plurality of nodes of the computational domain; and
   estimating personalized tissue parameters of the bio-heat model and the cellular necrosis model that minimize the error between the simulated ablation results and the first observed ablation result.

5. The method of claim 4, wherein performing one or more virtual ablations for the patient using the bio-heat model with the personalized tissue parameters, comprises for each of the one or more virtual ablations:
   simulating heat diffusion due to the virtual ablation based on a virtual ablation probe position and the simulated blood flow in the liver and a circulatory system of the liver by solving the bio-heat model with the personalized tissue parameters at each of the plurality of nodes of the computational domain corresponding to the patient-specific anatomical model; and
   simulating cellular necrosis in the liver based on the simulated heat diffusion due to the virtual ablation using the cellular necrosis model with the personalized tissue parameters.

6. The method of claim 4, wherein simulating blood flow in the liver parenchyma and vessels based on the patient-specific anatomical model comprises:
   simulating the blood flow in the liver parenchyma and vessels using a computational fluid dynamics (CFD)-porous model in which a porous force at each node of the computational domain corresponding to the patient-specific anatomical model depends on a porosity value, wherein nodes belonging to the vessels have a first porosity value and nodes belonging to the liver parenchyma have a second porosity value.

7. The method of claim 6, wherein simulating the blood flow in the liver parenchyma and vessels using a computational fluid dynamics (CFD)-porous model in which a porous force at each node of the computational domain corresponding to the patient-specific anatomical model depends on a porosity value comprises:
   solving the CFD-porous model at each of the plurality of nodes of a level-set representation of the patient-specific anatomical model using a Lattice-Boltzmann method (LBM).

8. The method of claim 4, wherein simulating the heat diffusion due to an ablation based on a virtual ablation probe position and the simulated blood flow in the liver parenchyma and vessels by solving the bio-heat model at each of a plurality of nodes of a computational domain corresponding to the patient-specific anatomical model of the liver parenchyma and vessels comprises:
   solving the bio-heat model at each of the plurality of nodes of a level-set representation of the patient-specific anatomical model using a Lattice-Boltzmann method (LBM).

9. The method of claim 8, wherein solving the bio-heat model at each of the plurality of nodes of a level-set representation of the patient-specific anatomical model using a Lattice-Boltzmann method (LBM) comprises:
for each of the plurality of nodes:
calculating a temperature at each of a plurality of time steps by solving a first bio-heat model having a first cooling term if the node belongs to the vessels, and a second bio-heat model having a second cooling term if the node belongs to the liver parenchyma.

10. The method of claim 9, wherein the first bio-heat model is a Pennes bio-heat model and the second bio-heat model is a Wulff-Klinger bio-heat model.

11. The method of claim 4, wherein simulating cellular necrosis in the liver based on the simulated heat diffusion using a cellular necrosis model that computes a cellular state at each of the plurality of nodes of the computational domain comprises:
calculating the cellular state for each of the plurality of nodes of the computational domain at each of a plurality of time steps based on a respective calculated temperature at each of the plurality of nodes at each of the plurality of time steps; and
updating a heat capacity at each of the plurality of nodes at each of the plurality of time steps based on the calculated cellular state.

12. The method of claim 4, wherein the virtual ablation probe position is a position corresponding to a position of an ablation probe in the first actual ablation procedure from which the first observed ablation result was generated and deployment and device parameters of the virtual ablation probe correspond to the deployment and device parameters of the ablation probe in the first actual ablation procedure from which the first observed ablation result was generated.

13. The method of claim 1, further comprising:
generating a visualization of a temperature map of the liver for each of the one or more virtual ablations.

14. The method of claim 1, wherein the first observed ablation result comprises an observed necrosis region resulting from the first actual ablation procedure, the simulated ablation results generated using the bio-heat model comprise a simulated necrosis region, and estimating personalized tissue parameters for a bio-heat model that simulates blood flow in the liver parenchyma and vessels, heat diffusion, and cellular necrosis in the liver by adjusting one or more tissue parameters of the bio-heat model to minimize an error between simulated ablation results generated using the bio-heat model and the first observed ablation result comprises:
estimating personalized tissue parameters for the bio-heat model and a cellular necrosis model that minimize an error between the observed necrosis region and the simulated necrosis region.

15. The method of claim 14, wherein estimating personalized tissue parameters for the bio-heat model and a cellular necrosis model that minimize an error between the observed necrosis region and the simulated necrosis region comprises:
iteratively optimizing one or more tissue parameters of the bio-heat model and the cellular necrosis model to minimize the error between the observed necrosis region and the simulated necrosis region.

16. The method of claim 14, wherein estimating personalized tissue parameters for the bio-heat model and a cellular necrosis model that minimize an error between the observed necrosis region and the simulated necrosis region comprises:
optimizing a tissue diffusivity parameter of the bio-heat model and a damage rate coefficient of the cellular necrosis model to minimize the error between the observed necrosis region and the simulated necrosis region.

17. The method of claim 1, wherein estimating a patient-specific anatomical model of a liver parenchyma and vessels from medical image data of the patient comprises:
estimating a patient-specific anatomical model of the liver including the liver parenchyma, at least one tumor, a hepatic vein, a vena cava, a portal vein, a hepatic artery and a biliary system.

\* \* \* \* \*